United States Patent [19]

Cincotta et al.

[11] 4,283,537

[45] Aug. 11, 1981

[54] THIAZINE-1,1-DIOXIDE AND ISOTHIAZOLE-1,1-DIOXIDE DERIVATIVES AND PROCESS FOR PREPARATION

[75] Inventors: Louis Cincotta; James W. Foley, both of Andover, Mass.

[73] Assignee: Polaroid Corporation, Cambridge, Mass.

[21] Appl. No.: 956,908

[22] Filed: Nov. 2, 1978

[51] Int. Cl.$^3$ .............................................. C07D 275/04
[52] U.S. Cl. ...................................... 546/94; 544/33; 544/62; 544/133; 544/135; 544/368; 544/58.7; 546/95; 546/209; 548/207; 260/239 R
[58] Field of Search .................. 544/33, 62, 133, 135, 544/368, 98, 58.7; 546/95, 94; 260/245.5, 302, 304, 243.3, 239 R, 244.4; 548/207

[56] References Cited

PUBLICATIONS

Abramouitch, R., J. Chem. Soc., Perkin Trans I, 1974, (22), p. 2589.
Mustafa, A., J. Chem. Soc., (1952), p. 1339.
Dutt, J. Chem. Soc., 121, p. 2389, (1922).
Beilstein, "Handbuch der Organishen Chemie", vol. 27, p. 534.

*Primary Examiner*—Nicholas S. Rizzo
*Attorney, Agent, or Firm*—Sybil A. Campbell

[57] ABSTRACT

In one embodiment, the present invention is concerned with 3,3-disubstituted sulfam(na)phthaleins wherein one of the 3-substituents is derived from a perhalomethylcarbinol-substituted phenol or 1-naphthol useful as intermediates in the preparation of certain N-acylated sulfam(na)phthalein compounds, which compounds find utility, e.g., as pH-sensitive indicator dyes or photographic light-screening dyes.

In another embodiment, the present invention is concerned with a method of synthesizing said sulfam(na)phthalein intermediates by reacting certain 3-substituted-benz[d]isothiazole-1,1-dioxides (or 3-substituted-naphtho[1,8-de]-1,2-thiazine-1,1-dioxides) and a 4-OLi-naphthyllithium compound or a 4-OLi-phenyllithium compound substituted in the 3-position with a lithiated perhalomethylcarbinol group.

26 Claims, No Drawings

THIAZINE-1,1-DIOXIDE AND ISOTHIAZOLE-1,1-DIOXIDE DERIVATIVES AND PROCESS FOR PREPARATION

BACKGROUND OF THE INVENTION 1. Field of the Invention

This invention relates to 3,3-disubstituted-2,3-dihydrobenz[d]isothiazole-1,1-dioxides and to 3,3-disubstituted-2,3-dihydronaphtho[1,8-de]-1,2-thiazine-1,1-dioxides useful in the preparation of sulfam(na)phthaleins derived from certain perhalomethylcarbinol-substituted phenols and 1-naphthols and to the preparation of said 3,3-disubstituted compounds.

2. Description of the Prior Art

Various procedures have been reported for synthesizing 3-substituted-benz[d]isothiazole-1,1-dioxides and 3,3-disubstituted-2,3-dihydrobenz[d]isothiazole-1,1-dioxides from saccharin (3-oxo-2,3-dihydrobenz[d]isothiazole-1,1-dioxide) and from saccharin pseudo-chloride (3-chlorobenz[d]isothiazole-1,1-dioxide). As reported by A. Mustafa et al, *J. Chem. Soc.*, 1952, p. 1339, the treatment of saccharin pseudo-chloride with excess phenylmagnesium bromide gave the corresponding 3,3-diphenyl-2,3-dihydrobenz[d]isothiazole-1,1-dioxide in almost quantitative yield. Methyl-, ethyl-, n-propyl- and n-butylmagnesium halides were reported by these authors to react analogously. R. A. Abramovitch et al, *J. Chem. Soc., Perkin Trans I*, 1974(22), p. 2589, reviewed and reinvestigated the reactions of saccharins with alkyl and aryl Grignard reagents and found that either the 3-alkyl (or 3-aryl) -benz[d]-isothiazole-1,1-dioxide and/or the open-chain tertiary alcohol, o-$CH_2OH$ benzenesulfonamide wherein R is alkyl (or aryl) were obtained with one exception. When saccharin was treated with an excess of phenylmagensium bromide in boiling tetrahydrofuran, 3,3-diphenyl-2,3-dihydrobenz[d]isothiazole-1,1-dioxide was obtained as the minor product together with the open-chain tertiary alcohol.

R. A. Abramovitch et al also investigated the reaction of saccharin and saccharin pseudo-chloride with organolithium compounds and found that the reaction of saccharin with alkyl- and aryllithium compounds, such as, n-butyllithium and p-methoxyphenyllithium in tetrahydrofuran at −78° C. gave the corresponding 3-substituted-benz[d]-isothiazole-1,1-dioxide, exclusively. In addition to this general method for synthesizing 3-alkyl (or 3-aryl)-benz[d]-isothiazole-1,1-dioxides, the authors reported that the reaction of the pseudo-chloride with organolithium compounds, such as, n-butyllithium in tetrahydrofuran at −78° C. gave the corresponding 3,3-disubstituted-2,3-dihydrobenz[d]-isothiazole-1,1-dioxide as the major product.

Besides the reactions with Grignard and organolithium reagents, Friedel-Crafts reactions with the saccharins also have been disclosed. Dutt, *J. Chem. Soc.*, 121, p. 2389 (1922) reported that condensation of saccharin with aromatic amines and phenols in the presence of concentrated sulfuric acid and also in the presence of fused zinc chloride. The resulting condensation products with saccharin were named "sulfamphthaleins" by analogy to "phthaleins" and "sulfonephthaleins". Though the structure of 3,3-di(4'-hydroxyphenyl)-2,3-dihydrobenz[d]isothiazole-1,1-dioxide (named "phenolsulfamphthalein") was assigned to the condensation product obtained with saccharin and phenol, it has been determined that the compound corresponding to the proposed structure has properties different from those reported, for example, colorless rather than pink in alkali and also, that the compound corresponding to the structure given could not be synthesized by repeating the procedures reported by Dutt.

Copending U. S. patent application Ser. No. 836,010 of Stanley M. Bloom, Alan L. Borror and James W. Foley filed Sept. 23, 1977 is directed to a method of synthesizing phenol and 1-naphthol sulfamphthaleins and sulfamnaphthaleins possessing a carbonyl group in the 2-position of the sulfam(na)phthalein ring. As disclosed and claimed therein, the method of preparing these compounds comprises reacting a 3-(4'-OP-1'-phenyl/4'-OP-1'-naphthyl)-3-(phenyl/naphthyl)-2,3-dihydrobenz[d]isothiazole-1,1-dioxide (or 2,3-dihydronaphtho[1,8-de]-1,2-thiazine-1,1-dioxide) wherein P is a protecting group with a carboxylic acid halide to yield the corresponding 2-carbonyl derivative followed by removing the protecting group with weak acid to yield the product.

The 3-(4'-OP-1'-phenyl/4'-OP-1'-naphthyl)-3-(phenyl/naphthyl)-2,3-dihydrobenz[d]isothiazole-1,1-dioxides employed as starting materials in the above method may be synthesized by reacting a 3-(4'-OP-1'-phenyl/4'-OP-1'-naphthyl)benz[d]-isothiazole-1,1-dioxide and a phenyllithium or a naphthyllithium reagent as disclosed and claimed in copending U. S. patent application Ser. No. 836,008 of Alan L. Borror, Louis Cincotta, James W. Foley and Marcis M. Kampe filed Sept. 23, 1977. As discussed therein, the 3-(4'-OP-1'-phenyl/4'-OP-1'-naphthyl)benz[d]isothiazole-1,1-dioxides are prepared by blocking the functional hydroxy group and any substituent group(s), as may be appropriate, of the selected 4-halophenol or 4-halo-1-naphthol and converting the blocked phenol or 1-naphthol to the corresponding Grignard or lithium reagent which is then reacted with a saccharin reagent. The phenyl- or naphthyllithium reagent reacted with the 3-(4'-OP-1'-phenyl/4'-OP-1'-naphthyl)benz[d]isothiazole-1,1-dioxide may be substituted or unsubstituted and may be prepared from the corresponding halo-substituted compound by reacting with lithium metal or n-butyllithium to yield the lithium reagent. If substituents, such as, hydroxy, are present, they are blocked with the appropriate protecting group to render them compatible with organometallic reagents prior to conversion to the lithium compound. The protecting groups selected should be removable under mildly acidic conditions so that the blocked substituents can be regenerated simultaneously with the regeneration of the functional —OH group of the 4'-OP-1'-phenyl or 4'-OP-1'-naphthyl moiety. Starting materials for use in the method of aforementioned application Ser. No. 836,010 also may be prepared according to the method of copending U.S. patent application Ser. No. 836,025 of Alan L. Borror, James W. Foley, Marcis M. Kampe and John W. Lee, Jr. filed Sept. 23, 1977, which comprises reacting a 3-(phenyl/naphthyl)-benz[d]isothiazole-1,1-dioxide and a 4'-OP-phenyl/4'-OP-naphthyllithium compound to give the corresponding 3-(phenyl/naphthyl)-3-(4'-OP-1'-phenyl/4'-OP-1'-naphthyl)-2,3-dihydrobenz[d]isothiazole-1,1-dioxide wherein P represents a protecting group compatible with organometallic reagents which is capable of being removed in weak acid to regenerate the free —OH.

The present invention is concerned with a method of reacting a certain class of unprotected phenols and 1-naphthols with a 3-substituted-benz[d]isothiazole-1,1-dioxide or a 3-substituted-naphtho[1,8-de]-1,2-thiazine-1,1-dioxide and to the corresponding 3,3-disubstituted-2,3-dihydrobenz[d]isothiazole-1,1-dioxide (or 2,3-dihydronaphtho[1,8-de]-1,2-thiazine-1,1-dioxide)produced.

SUMMARY OF THE INVENTION

It is, therefore, one object of the present invention to provide a certain class of 3,3-disubstituted-2,3-dihydrobenz[d]isothiazole-1,1-dioxides (and 2,3-dihydronaphtho[1,8-de]-1,2-thiazine-1,1-dioxides).

It is another object of the present invention to provide a novel method of preparing said 3,3-disubstituted compounds.

Other objects of this invention will in part be obvious and will in part appear hereinafter.

This invention accordingly comprises the process involving the several steps and the relation and order of one or more of such steps with respect to each of the others and the product possessing the features, properties and the relation of elements which are exemplified in the following detailed disclosure and the scope of the application of which will be indicated in the claims.

According to the present invention, it has been found that certain phenols and 1-naphthols, namely, phenols and 1-naphthols substituted in the 2-position with a perhalomethylcarbinol group can be reacted with a 3-substituted-benz[d]isothiazole-1,1-dioxide to give the 3,3-disubstituted isothiazole without using a protecting group, e.g., methoxymethyl for blocking the phenolic (or naphtholic) and carbinol —OH groups. This is accomplished by reacting these phenols and 1-naphthols as the "lithiated" derivatives as will be described below. That the "lithiated" perhalomethylcarbinol-substituted phenols and 1-naphthols can be reacted in this manner to give the 3,3-disubstituted isothiazole is quite unexpected, since attempts to react the "lithiated" derivatives of phenols, such as, 4-OLi-3,5-dimethylphenyllithium and 4-OLi-3,5-dimethoxyphenyllithium with a 3-substituted-benz[d]isothiazole-1,1-dioxide to give the 3,3-disubstituted 2,3-dihydrobenz[d]isothiazole-1,1-dioxide were unsuccessful.

For a fuller understanding of the nature and objects of the present invention, reference should be had to the following detailed description.

DETAILED DESCRIPTION OF THE INVENTION

Specifically, the method of the present invention comprises reacting (a) a carbocyclic aryllithium compound selected from a 4-OLi-naphthyllithium compound substituted in the 3-position with a group,

wherein $R^I$ is perhalomethyl and $R^{II}$ is hydrogen or perhalomethyl and a 4-OLi-phenyllithium compound substituted in the 3-position with a group,

wherein $R^I$ is perhalomethyl and $R^{II}$ is hydrogen or perhalomethyl and (b) a compound selected from a 3-substituted-benz[d]isothiazole-1,1-dioxide wherein said 3-substituent is a phenyl moiety or a naphthyl moiety provided said 3-substituent is a phenyl moiety when said carbocyclic aryllithium compound is said 4-OLi-naphthyllithium compound and a 3-substituted-naphtho[1,8-de]-1,2-thiazine-1,1-dioxide wherein said 3-substituent is a phenyl moiety or a naphthyl moiety provided said 3-substituent is a phenyl moiety when said carbocyclic aryllithium compound is said 4-OLi-naphthyllithium compound in an inert organic solvent at a temperature between about −80° C. and 50° C. to give (c) a 3,3-disubstituted-2,3-dihydrobenz[d]isothiazole-1,1-dioxide or a 3,3-disubstituted-2,3-dihydronaphtho[1,8-de]-1,2-thiazine-1,1-dioxide wherein one of the 3,3 substituents is a 4'-OH-1'-naphthyl moiety substituted in the 3'-position with

wherein $R^I$ and $R^{II}$ have the same meaning given above or a 4'-OH-1'-phenyl moiety substituted in the 3'-position with

wherein $R^I$ and $R^{II}$ have the same meaning given above and the other of the 3,3-substituents is a phenyl moiety or a naphthyl moiety. Preferably, the halo substituents of said perhalomethyl are fluoro and/or chloro.

It will be understood that the 3,3-substituents and/or the ring-closing moiety of the compounds produced according to the subject method may contain one or more substituents in addition to those specified, which substituents should not interfere with the intended use of the compounds.

Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as phenyl and naphthyl; alkaryl and aralkyl, preferably, alkyl-substituted phenyl and phenyl-substituted alkyl, such as p-ethylphenyl, p-octylphenyl, p-dodecylphenyl, benzyl, phenethyl, phenylhexyl and phenyldodecyl; alkoxy, such as, methoxy, ethoxy, butoxy, octadecyloxy, 1-ethoxy-2-(β-ethoxyethoxy); aryloxy, such as, phenoxy, benzyloxy and naphthoxy; alkoxyalkyl, such as, methoxymethyl, ethoxymethyl, and dodecyloxyethyl; halo, such as, fluoro, bromo and chloro; trihalomethyl, such as trifluoromethyl and trichloromethyl; sulfonamido (—NHSO₂R° wherein R' is alkyl, aryl, alkaryl or aralkyl); sulfamoyl (—SO₂—NH—R° wherein R° has the same meaning given above); acyl (

wherein R° has the meaning given above); sulfonyl (—SO₂—R° wherein R° has the same meaning given above); sulfo; cyano; carboxy, hydroxy; and amino including mono- and disubstituted amino (—NR'R" wherein R' and R" each are hydrogen, alkyl, aryl, alkaryl or aralkyl and R' and R" taken together represent the atoms necessary to complete a saturated heterocyclic ring, such as piperidino, pyrrolidino, N-lower alkylpiperazino, morpholino, thiomorpholino and tetrahydro-2H,4H-1,3,6-dioxazocino or a fused heterocyclic ring system, e.g., quinolizidine.)

Tne novel intermediates of the present invention may be represented by the formula

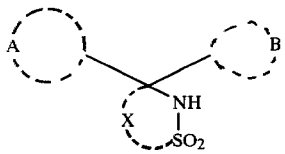 (I)

wherein A is selected from a 4'-hydroxy-1'-naphthyl moiety substituted in the 3'-position with a group,

wherein $R^I$ is perhalomethyl and $R^{II}$ is hydrogen or perhalomethyl and a 4'-hydroxy-1'-phenyl moiety substituted in the 3'-position with a group,

wherein $R^I$ is perhalomethyl and $R^{II}$ is hydrogen or perhalomethyl; B is a phenyl moiety or a naphthyl moiety provided B is a phenyl moiety when said A is said 4'-hydroxy-1'-naphthyl moiety and X represents the atoms necessary to complete a ring-closing moiety selected from 2,3-dihydrobenz[d]isothiazole-1,1-dioxide and 2,3-dihydronaphthao[1,8-de]-1,2-thiazine-1,1-dioxide.

In a preferred embodiment, the method of the present invention comprises reacting (a) a compound of the formula

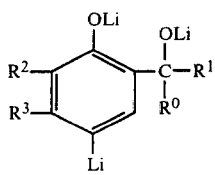

wherein $R^0$ is perhalomethyl selected from trifluoromethyl, difluoromethyl, difluorochloromethyl, dichlorofluoromethyl, dichloromethyl and trichloromethyl; $R^1$ is hydrogen or perhalomethyl having the same meaning given above; $R^2$ is hydrogen or methyl; $R^3$ is hydrogen, alkyl or alkoxy; $R^2$ and $R^3$ taken together represent the carbon atoms necessary to complete a fused benzene ring; and (b) a compound of the formula

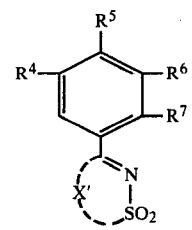

wherein $R^4$ and $R^6$ each are hydrogen, alkyl, alkoxy, chloro or fluoro; $R^5$ is hydrogen, alkyl, alkoxy, —$OP^I$ wherein $P^I$ is a protecting group, —N,N-(dialkyl)amino, —N,N-(w-$R^8$alkyl)$_2$—amino wherein $R^8$ is halo or —$OP^{II}$ wherein $P^{II}$ is a protecting group; —NH-COCH$_3$, piperidino, pyrrolidino, N-methylpiperazino, morpholino, thiomorpholino or tetrahydro-2H,4H-1,3,6-dioxazocino; $R^7$ is hydrogen, alkyl, alkoxy or —$OP^{III}$ wherein $P^{III}$ is a protecting group usually the same as $P^I$ or $P^{II}$; $R^6$ and $R^7$ taken together represent the carbon atoms necessary to complete a fused benzene ring provided $R^2$ and $R^3$ are taken separately when $R^6$ and $R^7$ are taken together; $R^4$, $R^5$ and $R^6$ taken together represent the atoms necessary to complete a fused [ij]-quinolizidine ring; and X' represents the atoms necessary to complete benz[d]isothiazole-1,1-dioxide or naphtho[1,8-de]-1,2-thiazine-1,1-dioxide in an inert organic solvent at a temperature between about −80° C. and 50° C. to give (c) the compound having the formula

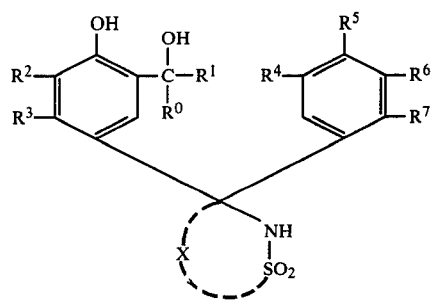

wherein $R^0$, $R^1$, $R^2$, $R^3$, $R^4$, $R^5$, $R^6$ and $R^7$ have the same meaning given above and X represents the atoms necessary to complete 2,3-dihydrobenz[d]isothiazole-1,1-dioxide or 2,3-dihydronaphtho[1,8-de]-1,2-thiazine-1,1-dioxide.

Usually, the alkyl and alkoxy substituents comprising $R^3$, $R^4$, $R^5$, $R^6$ and $R^7$ are lower alkyl having 1 to 4 carbon atoms, such as, methyl, ethyl, n-propyl, isopropyl and n-butyl and lower alkoxy having 1 to 4 carbon atoms, such as, methoxy, ethoxy, propoxy and butoxy. Also, the alkyl groups of the —N,N-(dialkyl)amino each are usually alkyl containing 1 to 4 carbon atoms; the alkyl groups of the —N,N-(w-$R^8$alkyl)$_2$amino usually are lower alkyl having 1 to 4 carbon atoms; and $R^8$, when halo, is preferably chloro. The perhalomethyl groups comprising $R^0$ and $R^1$ may be the same or different and usually are the same.

In a particularly preferred embodiment, X represents the atoms necessary to complete 2,3-dihydrobenz[d]isothiazole-1,1-dioxide.

The above reaction scheme is illustrated below using as specific reactants, 3-(9'-julolidinyl)benz[d]isothiazole-1,1-dioxide and the "lithiated" derivative of 1-naphthol substituted in the 2-position with bis trifluoromethylcarbinol, i.e., the lithiated derivative of [2-(α-hydroxy-α-trifluoromethyl-β,β,β-trifluoroethyl)-1-naphthol].

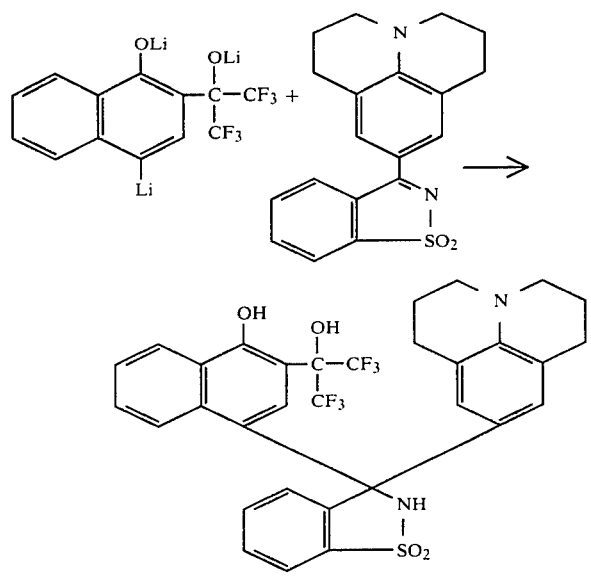

The novel intermediates produced in accordance with the subject method are those of formula I above and find utility as intermediates in the preparation of certain N-acylated sulfamphthaleins and sulfamnaphthaleins which, in turn, find utility as pH-sensitive indicator dyes, light-screening dyes and so forth.

By "sulfamphthalein" is intended a 2,3-dihydrobenz[d]isothiazole-1,1-dioxide moiety and by "sulfamnaphthalein" is intended a 2,3-dihydronaphtho[1,8-de]-1,2-thiazine-1,1-dioxide moiety. The respective 2,3-dihydrobenz[d]isothiazole-1,1-dioxide and 2,3-dihydronaphtho[1,8-de]-1,2-thiazine-1,1-dioxide ring-closing moieties are illustrated below:

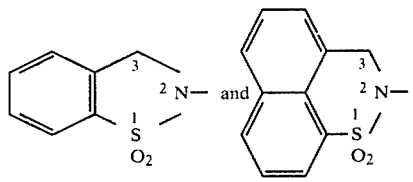

In a preferred embodiment, the compounds of the present invention may be represented by the formula

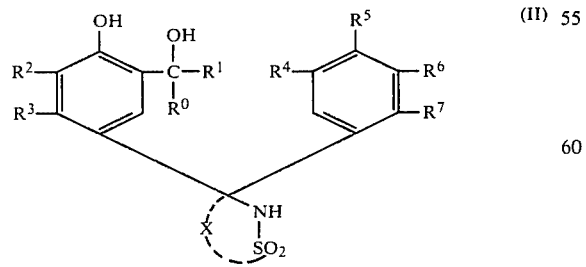

wherein $R^0$ is perhalomethyl selected from trifluoromethyl, difluoromethyl, difluorochloromethyl, dichlorofluoromethyl, dichloromethyl and trichloromethyl; $R^1$ is hydrogen or perhalomethyl having the same meaning given above; $R^2$ is hydrogen or methyl; $R^3$ is hydrogen, alkyl or alkoxy; $R^2$ and $R^3$ taken together represent the carbon atoms necessary to complete a fused benzene ring; $R^4$ and $R^6$ each are selected from hydrogen, alkyl, alkoxy, chloro and fluoro; $R^5$ is hydrogen, alkyl, alkoxy, $-OP^I$ wherein $P^I$ is a protecting group, $-N,N$-(dialkyl)amino, $-N,N$-(w-$R^8$alkyl)$_2$amino wherein $R^8$ is halo or $-OP^{II}$ wherein $P^{II}$ is a protecting group; $-NHCOCH_3$, piperidino, pyrrolidino, N-methylpiperazino, morpholino, thiomorpholino or tetrahydro-2H,4H-1,3,6-dioxazocino; $R^7$ is hydrogen, alkyl, alkoxy or $-OP^{III}$ wherein $P^{III}$ is a protecting group usually the same as $P^I$ or $P^{II}$; $R^6$ and $R^7$ taken together represent the carbon atoms necessary to complete a fused benzene ring provided $R^2$ and $R^3$ are taken separately when $R^6$ and $R^7$ are taken together; and $R^4$, $R^5$ and $R^6$ taken together represents the atoms necessary to complete a fused [ij]quinolizidine ring; and X represents the atoms necessary to complete 2,3-dihydronaphtho[1,8-de]-1,2-thiazine-1,1-dioxide and preferably, 2,3-dihydrobenz[d]isothiazole-1,1-dioxide.

Specific examples of compounds that may be prepared according to the method of the present invention are as follows:

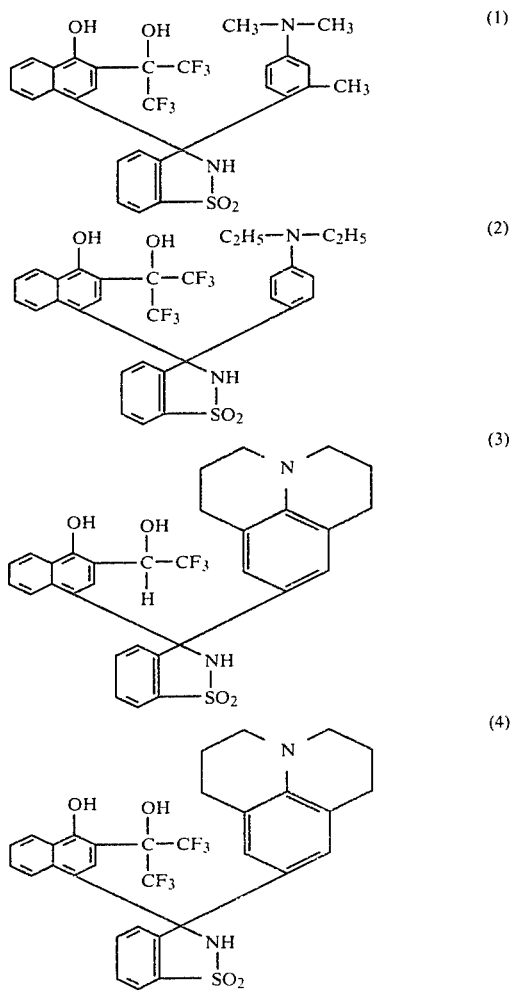

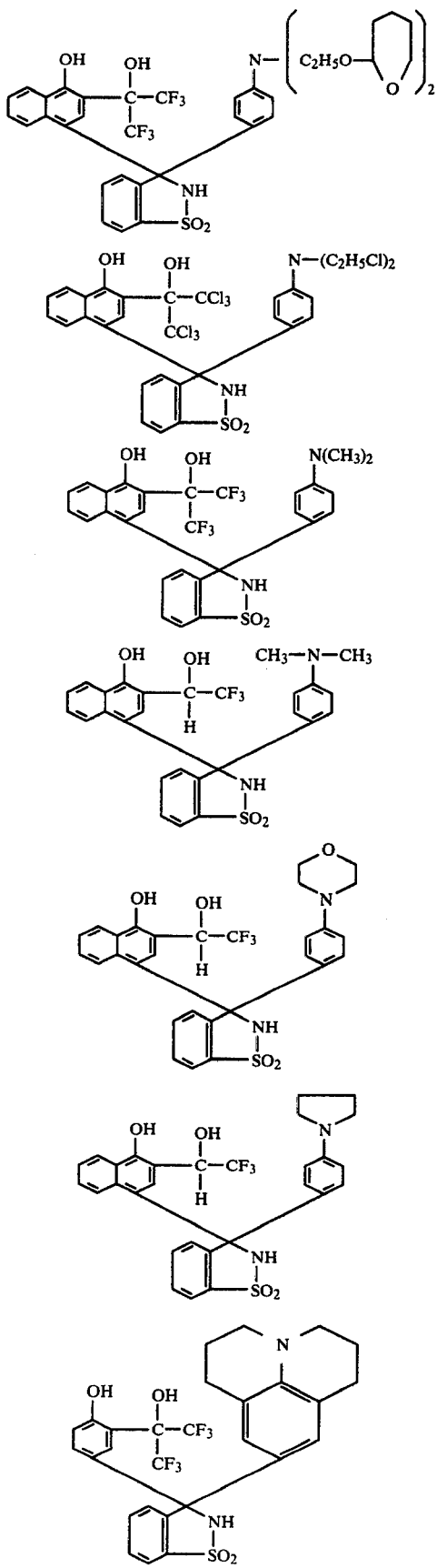
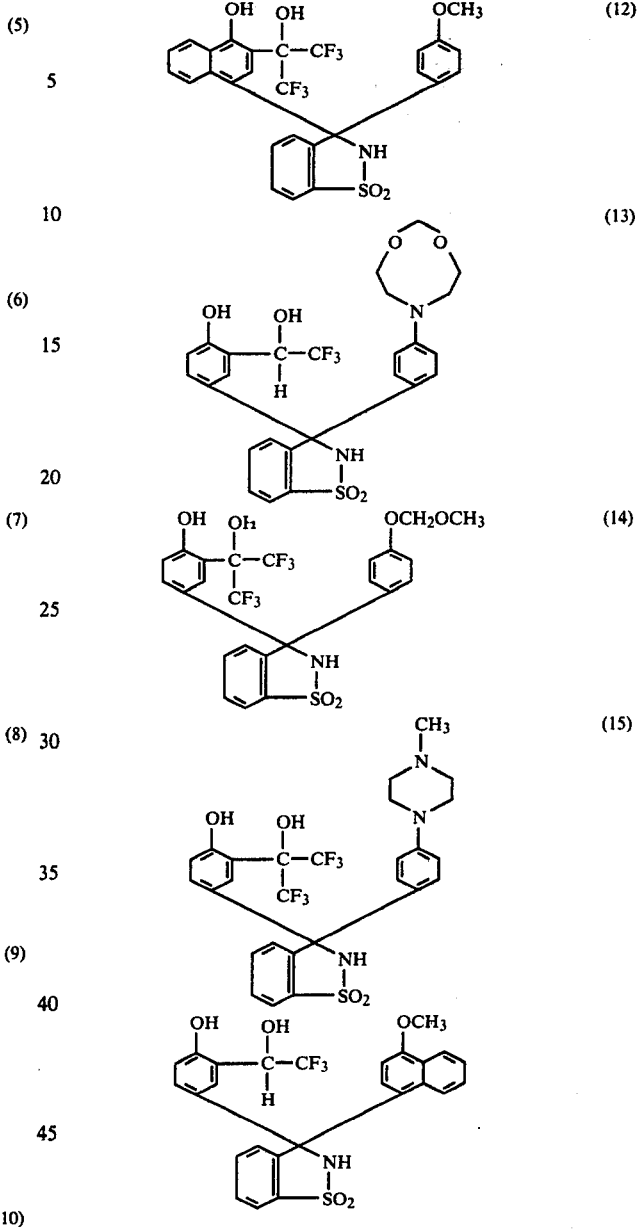

When 3-(4'-OP-1'-phenyl/4'-OP-1'-naphthyl)-benz[d]isothiazole-1,1-dioxides are employed as starting materials in the subject method, they are prepared by blocking the functional hydroxy group and any substituent group(s), as may be appropriate, of the selected 4-halophenol or 4-halo-1-naphthol and converting the blocked phenol or 1-naphthol to the corresponding Grignard or lithium reagent which is then reacted with a saccharin reagent. The 4-halo substituent may be chloro, bromo or iodo when the lithium reagent is prepared by reacting the blocked phenol or blocked 1-naphthol with lithium metal and is either bromo or iodo when the lithium reagent is made via a lithium exchange reaction using, for example, n-butyllithium. In preparing the Grignard reagent by reacting the blocked phenol or 1- naphthol with magnesium metal, the 4-halo substituent may be chloro, bromo or iodo. The Grignard or lithium reagent thus prepared is then reacted with saccharin, the N-lithium salt of saccharin or saccharin pseudo-chloride to yield the corresponding 3-(4'-OP-1'-phenyl/4'-OP-1'-naphthyl)benz[d]isothiazole-1,1-dioxide. Generally, the Grignard reagent is reacted with the pseudo-chloride, and the lithium reagent is reacted with the N-lithium salt. The 3-(4'-OP-1'-phenyl/4'-OP-1'-naphthyl)naphtho[1,8-de]-1,2-thiazine-1,1-dioxides may be prepared in a similar manner by reacting the Grignard or lithium reagent with 2,3-dihydro-3-oxo-naphtho[1,8-de]-1,2-thiazine-1,1-dioxide, its pseudo-chloride or the N-lithium derivative thereof.

The groups selected for protecting the functional phenolic or naphtholic hydroxy group and other hydroxy groups that may be present in the phenol or 1-naphthol should be stable to and compatible with organolithium and Grignard reagents and should protect the hydroxy group(s) against reaction under the conditions encountered in preparing the starting materials for the subject method and in the subsequent synthesis of the aforementioned N-acylated sulfam(na)phthalein products. In addition, the protecting group selected should be capable of being easily removed under weakly acid conditions to regenerate the hydroxy group(s) without the removal of or adversely affecting the N-substituent or other substituents that may be present. Alkyl groups, such as methyl and ethyl, may be employed in those instances where they can be removed without removal of the N-substituent. Because they can be readily removed without disturbing the N-substituent or other substituents, the phenol or 1-naphthol preferably is protected with methoxymethyl, 2'-tetrahydropyranyl or dimethyl-t-butylsilyl. The blocked phenols and 1-naphthols employing these protecting groups may be prepared by methoxymethylation as described, for example, by Kaoru Fuji et al, *Synthesis*, 4, pp. 276–277 (1975), by tetrahydropyranylation as described, for example, by William E. Parham et al, *J. Amer. Chem. Soc.*, 70, pp. 4187–4189 (1948) or by silylating with dimethyl-t-butylsilyl chloride in the presence of imidazole as described by E. J. Corey et al, *J. Amer. Chem. Soc.*, 94, pp. 6190–6191 (1972).

When the starting materials are 3-(phenyl/naphthyl)-benz[d]isothiazole-1,1-dioxides, i.e., other than 3-(phenyl/naphthyl) compounds containing a 4'-OP substituent, they may be prepared in a similar manner by blocking hydroxy and/or other substituent group(s), as may be appropriate, of the selected halo-benzene or halo-naphthalene compound and converting the halo compound to the corresponding Grignard or lithium reagent which is then reacted with the saccharin reagent to give the corresponding 3-substituted-benz[d]isothiazole-1,1-dioxide.

The "lithiated" derivative of the perhalomethylcarbinol-substituted phenol or 1-naphthol is prepared by reacting the selected 4-halophenol or 4-halo-1-naphthol with at least three molar equivalents of lithium metal or preferably n-butyllithium as illustrated below

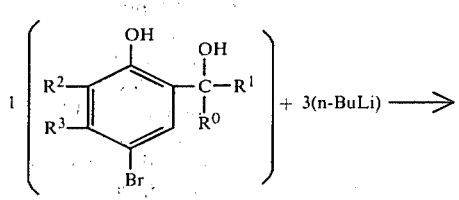

-continued

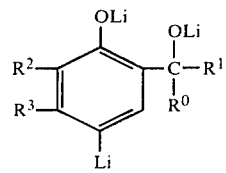

The perhalomethylcarbinol-substituted phenols and 1-naphthols may be prepared according to the procedures set forth by Basil S. Farah et al, *J. Org. Chem.*, Vol. 30, p. 1003 (1965) and are halogenated in any conventional manner to give the 4-halo derivatives, for example, by reacting the perhalomethylcarbinol-substituted compound with chlorine or bromine, with or without a catalyst; N-bromosuccinimide or iodinemonochloride.

Certain 3-(4'-OP-1'-phenyl/4'-OP-1'-naphthyl)benz[d]isothiazole-1,1-dioxides form the subject matter of copending U.S. patent application Ser. No. 836,024 of Alan L. Borror, L. Cincotta, E. W. Ellis, J. W. Foley and M. M. Kampe filed Sept. 23, 1977. 3-(Phenyl/naphthyl)benz[d]isothiazole-1,1-dioxides substituted with certain N-heterocyclic moieties form the subject matter of copending U.S. patent application Ser. No. 836,022 of Alan L. Borror, J. W. Foley and J. W. Lee, Jr. filed Sept. 23, 1977, and 3-(9'-julolidinyl)benz[d]isothiazole-1,1-dioxide forms the subject matter of copending U.S. patent application Ser. No. 836,023 also filed Sept. 23, 1977.

In carrying out the subject method, the selected 3-substituted-benz[d]isothiazole-1,1-dioxide is reacted with at least one molar equivalent of the "lithiated" phenol or 1-naphthol in an inert organic solvent, such as, benzene, diethyl ether, dioxane, hexane, toluene, petroleum ether or tetrahydrofuran. The reactants may be employed in equivalent, i.e., equimolar amounts but ordinarily an excess of about 0.1 to 1.0 mole of the "lithiated" phenol or 1-naphthol is employed per 1.0 mole of the 3-substituted-benz[d]isothiazole-1,1-dioxide. The reaction temperature may vary over a relatively wide range from about −80° to 50° C. as may be readily determined for the particular reactants. For achieving maximum yields, the reaction generally is conducted at a temperature below about 0° C. and preferably between about −65° C. and −25° C. As a matter of convenience, the 4-halo perhalomethylcarbinol-substituted phenol or 1-naphthol is reacted with the requisite amount of n-butyllithium at reduced temperatures of about −50° to −70° C. in an inert organic solvent such as those enumerated above to give the corresponding "lithiated" derivative and then the 3-substituted-benz[d]isothiazole-1,1-dioxide is added without isolating the "lithiated" derivative.

The following examples are given to further illustrate the present invention and are not intended to limit the scope thereof.

EXAMPLE 1

Preparation of the compound having the formula

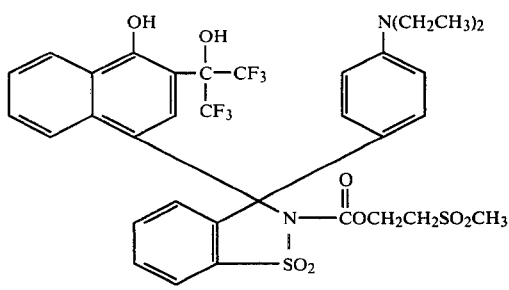

(a) 4-Bromo-2-(α-hydroxy-α-trifluoromethyl-β,β,β-trifluoroethyl)-1-naphthol (1.0 g) was dissolved in 25 ml tetrahydrofuran at room temperature under nitrogen, then cooled to −65° C. To this solution was added dropwise 3.21 ml of butyllithium (2.4 M in hexane). The resulting solution was stirred for one hour at −65° C. and then 3-(4′-N,N-diethylamino-1′-phenyl)benz[d]isothiazole-1,1-dioxide (0.51 g) was added, the solution warmed to −20° C., then cooled back to −65° C. and stirred for one hour. TLC on silica gel with ether showed that the reaction was complete. The reaction solution was poured into 200 ml. of water, the pH adjusted to 6 with conc. HCl and the resulting solution extracted with ether. The ether layer was separated and washed with 200 ml. of 1 N sodium hydroxide. The aqueous sodium hydroxide layer was separated, washed well with ether, then neutralized with conc. HCl and extracted with ether. The ether extract was dried over anhydrous sodium sulfate and evaporated to give 3-[(-3′-α-hydroxy-α-trifluoromethyl-β,β,β-trifluoroethyl)-4′-hydroxy-1′-naphthyl]-3-[4′-N,N-diethylamino-1′-phenyl]-2,3-dihydrobenz[d]isothiazole-1,1-dioxide as a green solid (0.82 g; 50% yield).

(b) The compound prepared in step (a) above (0.7 g) was dissolved in 25 ml pyridine at room temperature. To this was added 0.21 g of ClCOOCH2CH2SO2CH3 and the reaction mixture stirred for several hours. TLC on silica gel with ether indicated no apparent reaction. Thus, additional acid halide (0.42 g) was added and the mixture stirred overnight. The reaction mixture was poured into water, extracted with ether and the ether extract evaporated. The title compound was obtained as a blue compound from the ether residue by preparative TLC on silica gel.

The 3-(4′-N,N-diethylamino-1′-phenyl)benz[d]isothiazole-1,1-dioxide was prepared as follows:

4-Bromo-N,N-diethylaniline (22.8 g) was dissolved in 100 ml. of anhydrous tetrahydrofuran under nitrogen and then cooled to −74° C. To this solution was added dropwise 41.8 ml of n-butyllithium (2.4 M in hexane) over a 50-minute period. (The temperature was maintained at −70° C. during the addition.) The solution was stirred for one hour. Then a solution of the N-lithium salt of saccharin in 100 ml of tetrahydrofuran was added dropwise to the aniline solution at −70° C. using a double ended needle. The resulting reaction mixture was stirred for 4 hours, poured slowly into 1 liter of water and the pH adjusted to 6 with conc. HCl. An orange precipitate formed which was filtered, dried and dissolved in 250 ml of methanol containing about 5 ml of conc. HCl. The solution was refluxed for 30 minutes and the precipitate collected to give 14.0 g of the title compound (melting range 207°–208° C.).

EXAMPLE 2

Preparation of the compound having the formula

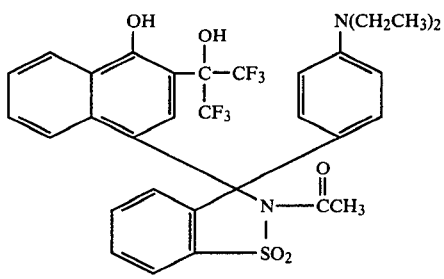

(a) 4-Bromo-2-(α-hydroxy-α-trifluoromethyl-β,β,β-trifluoroethyl)-1-naphthol (1.0 g) was dissolved in 20 ml of anhydrous tetrahydrofuran at room temperature. The solution was then cooled to −65° C., and 3.21 ml of n-butyllithium (2.4 M in hexane) was added dropwise (an exotherm occurred during approximately 1 ml of the addition). The resulting light yellow solution was then stirred for one hour at −65° C. To the solution was added 0.81 g of 3-(4′-N,N-diethylamino-1′-phenyl)-benz[d]isothiazole-1,1-dioxide. The reaction solution was allowed to warm to −40° C. then poured into 200 ml of water, made pH 6 with conc. HCl and extracted with ether. The ether was then washed with 200 ml of 1 N sodium hydroxide. The sodium hydroxide solution was separated, washed with ether, then neutralized with HCl. The neutralized solution was extracted with ether, the ether dried over sodium sulfate and evaporated to leave a light green solid. Preparative TLC on silica gel with ether gave 0.5 g of 3-[(3′-α-hydroxy-α-trifluoromethyl-β,β,β-trifluoroethyl)-4′-hydroxy-1′-naphthyl]-3-[4′-N,N-diethylamino-1′-phenyl]-2,3-dihydrobenz[d]isothiazole-1,1-dioxide.

(b) The compound prepared in step (a) (0.5 g) was dissolved in 25 ml of pyridine and 2 ml of acetylchloride was added dropwise at room temperature. The reaction solution was stirred for 6 hours, poured into 500 ml of water, and the tan precipitate was filtered, washed well with water and vacuum dried.

(c) The triacetylated compound prepared in step (b) was dissolved in 100 ml of methanol and 5 drops of 50% aqueous sodium hydroxide solution was added. The resulting purple solution was stirred for 2 hours. TLC on silica gel with ether showed that de-acetylation of the —OH groups was complete. The methanol was removed under vacuum. After neutralization with HCl, chloroform was added to the residue and sodium sulfate for drying. The solution was filtered and the chloroform evaporated to leave 0.584 g of the title compound as a cyan solid.

EXAMPLE 3

Preparation of the compound having the formula

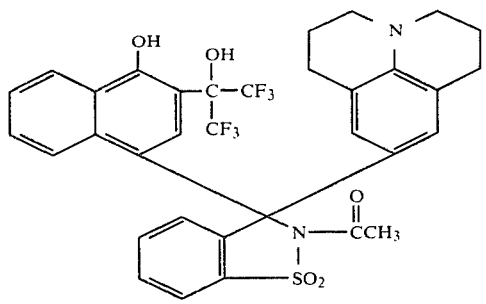

The title compound was prepared according to the procedure described in Example 2 above except that 4-bromo-2-(α-hydroxy-α-trifluoromethyl-β,β,β-trifluoroethyl)-1-naphthol and 3-(9'-julolidinyl)benz[d]isothiazole-1,1-dioxide were employed in step (a).

The 3-(9'-julolidinyl)benz[d]isothiazole-1,1-dioxide was prepared as follows:

(a) 134 g (0.758 mol) of 98% julolidine was dissolved in 500 ml of glacial acetic acid. To this solution was added a solution of 121 g (0.758 mol) of bromine in 2400 ml of glacial acetic acid. After the addition, the reaction mixture was stirred for 15 minutes and then tested for excess bromine using KI paper. More bromine was added until an excess was detected. The reaction mixture was then stirred for 1 hour at room temperature. The pink solid which formed was collected and washed several times with ether and dried in a vacuum oven overnight to give 245 g of the hydrobromide salt of 9-bromojulolidine. Yield 92% by weight.

(b) 75 g (0.22 mol) of 9-bromojulolidine hydrobromide prepared in step (a) was suspended in 1200 ml of ether. To the suspension was added 650 ml of 1 N sodium hydroxide and the mixture stirred for 5–10 minutes. The two layers were separated and the aqueous layer was extracted with 1000 ml of ether. The organic layers were combined, dried over anhydrous calcium sulfate and the ether evaporated to yield 51.97 g (0.206 mol) of 9-bromojulolidine as a dark oil.

(c) The 9-bromojulolidine was dissolved in 400 ml of dry tetrahydrofuran under nitrogen at −65° C. 85.8 ml of n-butyllithium (2.4 M in hexane) was added dropwise giving a tan slurry.

(d) 37.75 g (0.206 mol) of saccharin was dissolved in 400 ml of dry tetrahydrofuran under nitrogen at −65° C. 85.8 ml (0.206 mol) of n-butyllithium (2.4 M in hexane) was added dropwise until a permanent orange colored endpoint was reached. The mixture was stirred for 1 hour at −65° C. and then used directly in step (e).

(e) The mixture of step (d) was added to the tan slurry of step (c) at −60° C. to −50° C. through a double ended needle. After the addition was completed, the reaction mixture was stirred for 1 hour at −60° C. and gradually warmed to room temperature. The reaction mixture was then poured into 800 ml of water and the pH adjusted to 5–6 with conc. HCl. The orange precipitate which formed was collected to give 13.9 g of the title compound. The filtrate was extracted with ether, dried and evaporated to give 46 g of a dark oil. The oil was washed with hot hexane and then dissolved in hot ethanol (500 ml) and 75 drops of conc. HCl was added. The ethanol was cooled and 7.53 g of orange crystals were collected to give the title compound in a total yield of 21.47 g.

EXAMPLE 4

Preparation of the compound having the formula

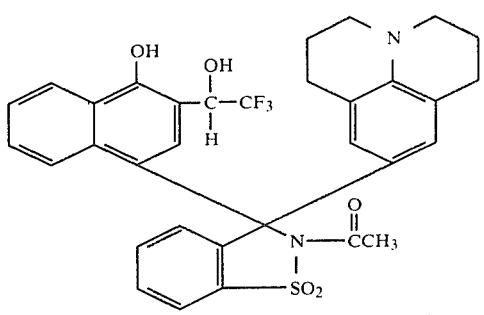

The title compound was prepared according to the procedure described in Example 2 above except that 4-bromo-2-(α-hydroxy-β, β,β-trifluoroethyl)-1-naphthol and 3-(9'-julolidinyl)benz[d]isothiazole-1,1-dioxide were employed in step (a).

EXAMPLE 5

Preparation of the compound having the formula

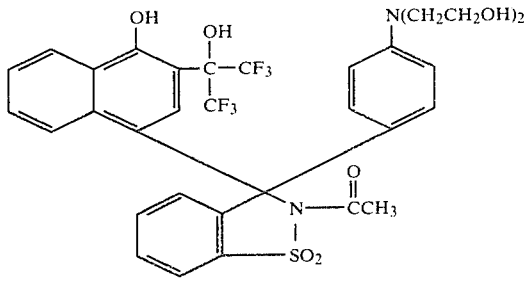

The title compound was prepared according to the procedure described in Example 2 above except that 4-bromo-2-(α-hydroxy-α-trifluoromethyl-β,β,β-trifluoroethyl)-1-naphthol and 3-[4'-N,N-di(β-2''-tetrahydropyranyloxyethyl)-1'-phenyl]benz[d]isothiazole-1,1-dioxide were employed in step (a) and the tetrahydropyranol protecting groups were removed subsequent to de-acetylation of the hydroxy groups by refluxing in methanol made acidic with conc. HCl for about one hour.

The 3-[4'-N,N-di(β-2''-tetrahydropyranyloxyethyl)-1'-phenyl]benz[d]isothiazole-1,1-dioxide was prepared as follows:

4-Bromo-N,N-di(β-2'-tetrahydropyranyloxyethyl)aniline (10.0 g) was dissolved in 100 ml of tetrahydrofuran. The solution was cooled to −65° C. and 10 ml of n-butyllithium (2.4 M in hexane) was added dropwise under nitrogen at a rate to maintain the temperature below −65° C.

In a separate flask, saccharin (4.28 g) was dissolved in 50 ml of tetrahydrofuran under nitrogen, and the solution was cooled to −65° C. n-Butyllithium (2.4 M in hexane) was added until a peach color persisted (about 9.0 ml).

The latter solution of the N-lithium salt of saccharin was added to the aniline solution by hollow wire over a 10 minute period. (Initially a green color formed which changed to tan.) The reaction mixture was stirred for 1.5 hours and poured into 2 liters of water. The pH was adjusted to 6 with conc. HCl, and the mixture extracted with ether. The ether extract was dried and evaporated and the residue was dissolved in 100 ml of toluene. Two spatula tips of toluene sulfonic acid monohydrate were added, and the solution was refluxed for about 6 hours. The toluene was evaporated and the residue was dissolved in 2 liters of ether. The ether solution was cooled and the crystalline solid was collected to give 4.0 g of the title compound (melting range 100°–101° C.).

Tetrahydropyranylation of p-Br-N,N-di(β-hydroxyethyl)aniline was carried out as follows:

p-Br-N,N-di(β-hydroxyethyl)aniline (20.0 g) was dissolved in 475 ml of dichloromethane containing 60 ml of dihydropyran. To this solution was added 1 ml of conc. HCl, and the reaction solution was stirred for about 5.5 hours. The solution was then washed with water containing enough sodium hydroxide to neutralize any acid present. The dichloromethane was separated, dried over anhydrous sodium sulfate and evaporated under reduced pressure with a steam bath (aspirator) leaving an oil. The oil was heated to 115° C. at 0.1 mm Hg to distill off impurities leaving 33.0 g of the title compound.

EXAMPLE 6

Preparation of the compound having the formula

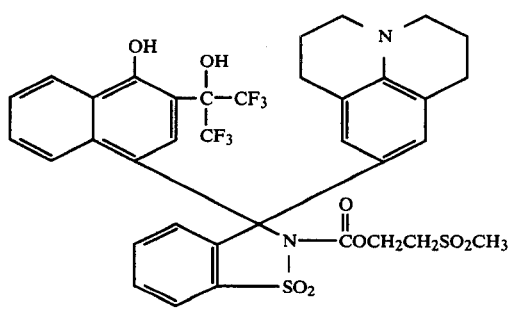

(a) 3-[(3'-α-hydroxy-α-trifluoromethyl-β,β,β-trifluoroethyl)-4'-hydroxy-1'-naphthyl]-3-(9'-julolidinyl)-2,3-dihydrobenz[d]isothiazole-1,1-dioxide was prepared according to the procedure given in Example 2 above except that 4-bromo-2-(α-hydroxy-α-trifluoromethyl-β,β,β-trifluoroethyl)-1-naphthol) and 3-(9'-julolidinyl)-benz[d]isothiazole-1,1-dioxide were employed in step (a).

(b) The compound prepared in step (a) (17.0 g) was dissolved in 400 ml of pyridine at room temperature under nitrogen. To this solution was added ½ pound of Type 3A molecular sieves. This was stirred mechanically in the dark and 30 g of β-(methylsulfonyl)ethylchloroformate was added and stirred for 3 hours. TLC on silica gel with 1:9 methanol/ether showed a trace of the starting isothiazole. The reaction mixture was filtered, washed with methylene chloride, poured into 5 liters of water and extracted with 1500 ml of methylene chloride. The methylene chloride was dried over sodium sulfate and evaporated under reduced pressure to remove all of the pyridine. The residue was washed with hexane several times and then vacuum dried to give 21.0 g of the title compound as a blue solid.

EXAMPLE 7

Preparation of the compound of the formula

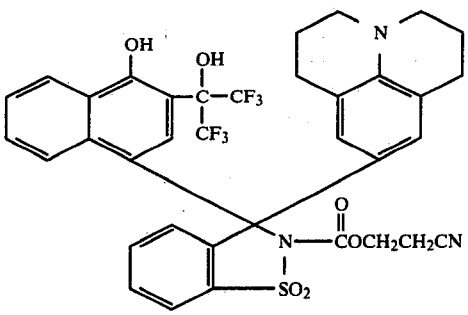

(a) 3-[(3'-α-hydroxy-α-trifluoromethyl-β,β,β-trifluoroethyl)-4'-hydroxy-1'-naphthyl]-3-(9'-julolidinyl)-2,3-dihydrobenz[d]isothiazole-1,1-dioxide was prepared according to the procedure given in Example 2 above except that 4-bromo-(3-α-hydroxy-α-trifluoromethyl-β,β,β-trifluoroethyl)-1-naphthol and 3-(9'-julolidinyl)-benz[d]isothiazole-1,1-dioxide were employed in step (a).

(b) The compound prepared in step (a) (1.5 g) was dissolved in 25 ml of pyridine; 3 g of acidic alumina was added; and then 1.0 ml of β-cyanoethylchloroformate was added. The resulting reaction mixture was stirred for 16 hours at room temperature. The yellow solution turned green to cyan. The alumina was removed from the pyridine by filtration. The filtrate was poured into 200 ml of water, extracted with ether and the ether dried over sodium sulfate and evaporated. The residue was purified by medium pressure column chromatography using a silica gel stationary phase and 5% methanol in methylene chloride as elutant. TLC of samples on silica gel with ether showed the title compound as a fairly pure product.

EXAMPLE 8

Preparation of the compound having the formula

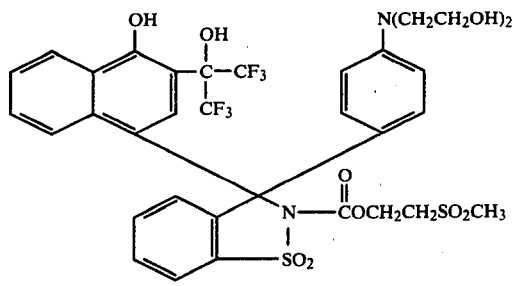

(a) 3-[3'-α-hydroxy-α-trifluoromethyl-β,β,β-trifluoroethyl-4'-hydroxy-1'-naphthyl]-3-[4'-N,N-di(β-2''-tetrahydropyranyloxyethyl)-1'-phenyl)benz[d]isothiazole-1,1-dioxide was prepared according to the procedure given in Example 2 above except that 4-bromo-2-(α-hydroxy-α-trifluoromethyl-β,β,β-trifluoroethyl)-1-naphthol and 3-[4'-N,N-di(β-2''-tetrahydropyranyloxyethyl)-1'-phenyl]benz[d]isothiazole-1,1-dioxide were employed in step (a).

(b) The compound prepared in step (a) (2.0 g) was dissolved in approximately 30 ml of pyridine. To this solution was added 20.0 g of Type 3A molecular sieves and 1.13 g of (β-methylsulfonyl)ethylchloroformate and then the reaction mixture was stirred vigorously at room temperature for 3 to 4 hours. TLC on silica gel using 80:20 hexane/acetone showed that a comparatively large amount of starting isothiazole was present. More (β-methylsulfonyl)ethylchloroformate (0.6 g) was added, and the mixture was stirred at room temperature overnight. The following morning only a trace of the starting isothiazole could be detected. The reaction mixture was poured into cold water overlayered with ethyl acetate. The ethyl acetate was decanted, washed with several portions of fresh water, dried over anhydrous sodium sulfate and the solvent removed leaving a dark blue, tacky residue. The residue was dried under vacuum in the presence of phosphorus pentoxide to yield 1.9 g of a dark blue solid.

The tetrahydropyranyl groups were removed by dissolving the blue solid in methanol, made acidic with conc. hydrochloric acid and refluxing for 1 hour. The methanol was removed by evaporation to yield the title compound.

4-Bromo-2-(α-hydroxy-α-trifluoromethyl-β,β,β-trifluoroethyl)-1-naphthol was prepared by adding a suspension of 50 g (0.161 mole) of 2-(α-hydroxy-α-trifluoromethyl)-1-naphthol in 500 ml of CCl₄ to a 3-necked, 2-liter flask equipped with a mechanical carrier. This suspension was stirred while a solution of 8.5 ml (0.161 mole) Br₂ in 200 ml CCl₄ was added dropwise. Upon completion of the addition, the mixture was stirred for 2 hours, then filtered, and the filtrate evaporated under reduced pressure to leave a tan solid. This solid was dissolved with heating on a steam bath into 300 ml of ligroin (b.p. 90°–110° C.). 10 Grams of norit was added, heating was continued for a further 10 minutes, and then the mixture was filtered through a sintered glass funnel containing a celite pad. Upon cooling and filtration, 50 g of white crystals were collected (melting range 116°–117° C.). The mother liquor was concentrated to one-half the original volume and a second crop of 5 g (melting range 112°–115° C.) was collected to give a total yield of 55 g (88%).

EXAMPLE 9

Preparation of the compound having the formula

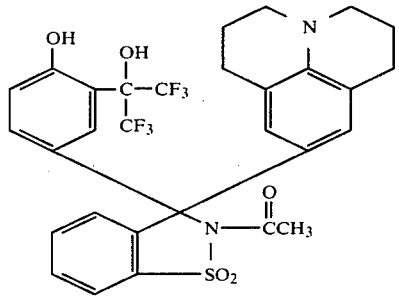

The title compound was prepared according to the procedure given in Example 2 above except that 4-bromo-2-(α-hydroxy-α-trifluoromethyl-β,β,β-trifluoroethyl)-1-phenol and 3-(9′-julolidinyl)benz[d]isothiazole-1,1-dioxide were employed in step (a).

EXAMPLE 10

Preparation of the compound having the formula

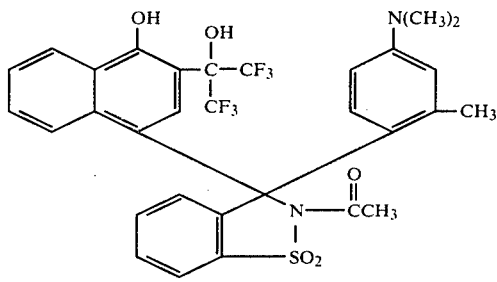

The title compound was prepared according to the procedure given in Example 2 above except that 4-bromo-2-(α-hydroxy-α-trifluoromethyl-β,β,β-trifluoroethyl)-1-naphthol and 3-(4′-N,N-dimethylamino-2′-methyl-1′-phenyl)benz[d]isothiazole-1,1-dioxide were employed in step (a).

EXAMPLE 11

Preparation of the compound of the formula

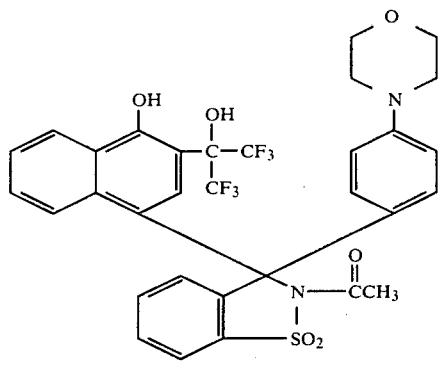

The title compound was prepared according to the procedure given in Example 2 above except that 4-bromo-2-(α-hydroxy-α-trifluoromethyl-β,β,β-trifluoroethyl)-1-naphthol and 3-(4′-N,N-dimethylamino-2′-methyl-1′-phenyl)benz[d]isothiazole-1,1-dioxide were employed in step (a).

Where it is desired to prepare sulfamnaphthaleins, it will be appreciated that 2,3-dihydro-3-oxo-naphtho[1,8-de]-1,2-thiazine-1,1-dioxide or its pseudo-chloride may be substituted for the saccharin reagents used in the foregoing Examples to give the corresponding sulfamnaphthalein intermediates and products. The pseudo-chloride may be prepared from the 3-oxo thiazine by reaction with PCl₅ as described above for the preparation of saccharin pseudo-chloride.

The method of reacting the subject compounds with

wherein W is chloro or bromo and Y is hydrogen or an electron-withdrawing group to give the corresponding

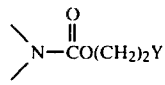

products from the subject matter of copending U.S. patent application Ser. No. 957,162 of Louis Cincotta and James W. Foley filed concurrently herewith. The method reacting the subject compounds with

wherein W is chloro or bromo and R is alkyl or phenyl to give the corresponding

compounds followed by selective removal of the

groups from the —OH groups with alkali forms the subject matter of copending U.S. patent application Ser. No. 956,907 of Louis Cincotta and James W. Foley filed concurrently herewith.

As discussed in applications Ser. Nos. 957,162 and 956,907, the compounds wherein the substituent on the N atom of the ring-closing moiety is

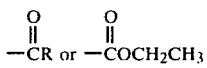

are useful as pH-sensitive indicator dyes and have reversibly alterable spectral absorption characteristics in response to changes in environmental pH. Besides their use in titrations and other analytical procedures where pH-sensitive indicator dyes are commonly employed, the compounds having a colorless form below a given pH may be used for providing colored optical filter agents in photographic products and processes where the pH is reduced subsequent to processing as described in U.S. Pat. No. 3,647,437 issued Mar. 7, 1972 to Edwin H. Land. This patent is concerned with diffusion transfer processes wherein the resulting photograph comprises the developed photosensitive layer(s) retained with the image-receiving layer as part of a permanent laminate. In the processes disclosed, a photographic film unit comprising a photosensitive element is developed in ambient light but further undesired exposure during processing is prevented by a light-absorbing material or optical filter agent which is retained in the processed film unit. In a preferred embodiment, the optical filter agent is a pH-sensitive dye, i.e., a dye possessing spectral absorption characteristics that are reversibly alterable in response to changes in environmental pH and particularly, a pH-sensitive dye having a colored or light-absorbing form above a given alkaline pH and a colorless or non-light-absorbing form below said pH. Though the pH-sensitive dye is usually included in the processing composition, it may be initially positioned in the film unit, for example, in a layer over the photosensitive element provided it is in its colorless form if photoexposure is to be effected through that layer. Upon application of an alkaline processing composition, the pH-sensitive dye is converted to its colored form, and after the desired processing time, it is converted back to its colorless form by reducing the environmental pH, e.g., by including an acid-reacting layer as part of the film unit.

Where the N-substituent is

and Y is an electron-withdrawing group, the compounds have a colored form in aqueous alkaline solution above a given alkaline pH and are discharged, i.e., decolorized independently of pH reduction by irreversible cleavage of the N-substituent after remaining in contact with said alkaline solution for a predetermined time. For example, the colored form generated from these compounds possessing a

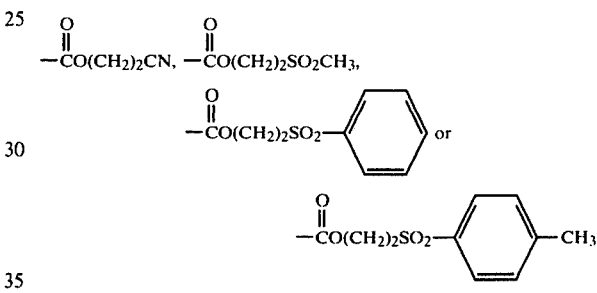

substituent on the N atom of the benz[d]isothiazole-1,1-dioxide moiety usually have a half-life (T ½) in approximately 1 N NaOH of about 30 seconds or less. By T ½ is meant the time measured for one-half of the colored form to decolorize. When these compounds are initially colorless, they may be employed as colorless precursors for providing colored photographic optical filter agents for protecting an imagewise exposed photosensitive material from further exposure during processing in light as described in copending U.S. patent application Ser. No. 836,006 of Stanley M. Bloom, Alan L. Borror and James W. Foley filed Sept. 23, 1977. In the processes disclosed, the colorless filter agent precursor is initially disposed in a layer of the film unit, for example, in a layer coated over the photosensitive element, and subsequent to imagewise exposure of the photosensitive element, the colored optical filter agent is generated by contacting the colorless precursor with base, e.g., an aqueous alkaline processing composition. After remaining in contact with said base for a given time, the colored optical filter agent is discharged by forming a new compound which is substantially colorless and which is different from and non-reversible by a pH change to either said optical filter agent or said precursor. When these compounds are initially colored, they may be employed as light-screening dyes in photographic products and processes, i.e., as antihalation dyes positioned, for example, between a photosensitive silver halide layer and the film base or support or as filter dyes, for example, in multi-layer, multicolor photographic materials to adjust the sensitometry for achieving the desired color balance. The use of these compounds as light-screening dyes in photographic products and processes is disclosed and claimed in copending U.S. patent application Ser. No. 957,161 of James W. Foley filed concurrently herewith. As described therein, a photographic film unit comprising a photosensitive material and a layer comprising these compound(s) as antihalation or filter dye(s) is exposed imagewise and then processed by applying an aqueous alkaline processing composition. After remaining in contact with said alkaline composition for a given time, the colored antihalation or filter dye is discharged by forming a new compound which is substantially colorless and which is different from and non-reversible by pH change to said dye.

3,3-Disubstituted-sulfamphthaleins and sulfamnaphthaleins wherein one of the 3-substituents is (a) a 4'-hydroxy-1'-naphthyl moiety substituted in the 3'-position with, e.g., a mono or bis perhalomethylcarbinol group; the other 3-substituent is, for example, a substituted phenyl moiety having certain electron-donating properties; and the N atom of the sulfam(na)phthalein ring is substituted with

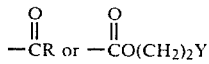

as defined above form the subject matter of copending U.S. patent application Ser. No. 957,163 of James W. Foley filed concurrently herewith.

For convenience, the specifications of aforementioned applications Ser. Nos. 836,006; 957,161; and 957,163 are specifically incoporated herein.

Since certain changes may be made in the above product and process without departing from the scope of the invention herein involved, it is intended that all matter contained in the above description shall be interpreted as illustrative and not in a limiting sense.

What is claimed is:

1. A method which comprises reacting (a) a compound of the formula

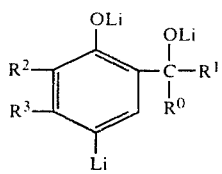

wherein $R^0$ is perhalomethyl selected from trifluoromethyl, difluoromethyl, difluorochloromethyl, dichlorofluoromethyl, dichloromethyl and trichloromethyl; $R^1$ is hydrogen or perhalomethyl having the same meaning given above; $R^2$ is hydrogen or methyl; $R^3$ is hydrogen, alkyl or alkoxy; $R^2$ and $R^3$ taken together represent the carbon atoms necessary to complete a fused benzene ring; and (b) a compound of the formula

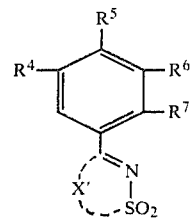

wherein $R^4$ and $R^6$ each are hydrogen, alkyl, alkoxy, chloro or fluoro; $R^5$ is hydrogen, alkyl, alkoxy, —$OP^I$ wherein $P^I$ is a protecting group, —N,N-(dialkyl)amino, —N,N-(w-$R^8$-alkyl)$_2$—amino wherein $R^8$ is halo or —$OP^{II}$ wherein $P^{II}$ is a protecting group; —NHCOCH$_3$, piperidino, pyrrolidino, N-methylpiperazino, morpholino, thiomorpholino or tetrahydro-2H,4-H-1,3,6-dioxazocino; $R^7$ is hydrogen, alkyl, alkoxy or —$OP^{III}$ wherein $P^{III}$ is a protecting group usually the same as $P^I$ or $P^{II}$; $R^6$ and $R^7$ taken together represent the carbon atoms necessary to complete a fused benzene ring provided $R^2$ and $R^3$ are taken separately when $R^6$ and $R^7$ are taken together; $R^4$, $R^5$ and $R^6$ taken together represent the atoms necessary to complete a fused [ij]-quinolizidine ring; and X' represents the atoms necessary to complete benz[d]isothiazole-1,1-dioxide or naphtho[1,8-de]-1,2-thiazine-1,1-dioxide in an inert organic solvent at a temperature between about −80° C. and 50° C. to give the corresponding reaction product and hydrolyzing said reaction product at pH 6 to give (c) the compound having the formula

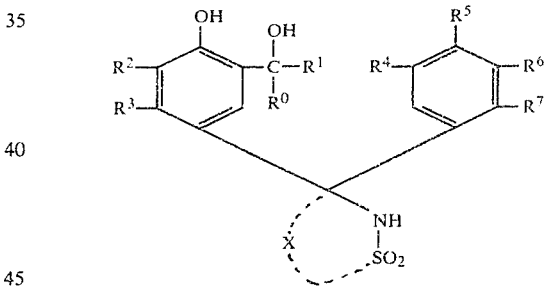

wherein $R^0$, $R^1$, $R^2$, $R^3$, $R^4$, $R^5$, $R^6$ and $R^7$ have the same meaning given above and X represents the atoms necessary to complete 2,3-dihydrobenz[d]isothiazole-1,1-dioxide or 2,3-dihydronaphtho[1,8-de]-1,2-thiazine-1,1-dioxide.

2. A method as defined in claim 1 wherein X' represents the atoms necessary to complete benz[d]isothiazole-1,1-dioxide.

3. A method as defined in claim 1 wherein $R^2$ and $R^3$ are hydrogen.

4. A method as defined in claim 1 wherein $R^2$ and $R^3$ taken together represent the carbon atoms necessary to complete a fused benzene ring.

5. A method as defined in claim 1 wherein $R^4$, $R^5$ and $R^6$ taken together represent the atoms necessary to complete a fused [ij]quinolizidine ring.

6. A method as defined in claim 1 wherein $R^4$, $R^6$ and $R^7$ are hydrogen.

7. A method as defined in claim 6 wherein $R^5$ is —N,N-(dialkyl)amino.

8. A method as defined in claim 6 wherein $R^5$ is —N,N-(w-$R^8$alkyl)amino.

9. A method as defined in claim 8 wherein $R^8$ is —$OP^{II}$.

10. A method as defined in claim 6 wherein $R^5$ is morpholino.

11. A method as defined in claim 1 wherein $R^1$ is hydrogen.

12. A method as defined in claim 1 wherein $R^1$ is perhalomethyl.

13. A method as defined in claim 1 wherein $R^0$ and $R^1$ are trifluoromethyl.

14. A compound of the formula

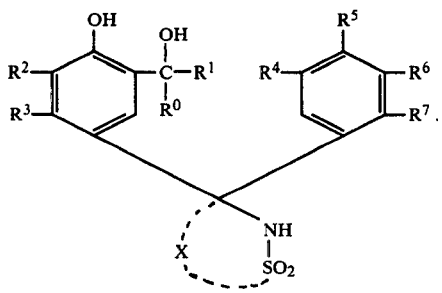

wherein $R^0$ is perhalomethyl selected from trifluoromethyl, difluoromethyl, difluorochloromethyl, dichlorofluoromethyl, dichloromethyl and trichloromethyl; $R^1$ is hydrogen or perhalomethyl having the same meaning given above; $R^2$ is hydrogen or methyl; $R^3$ is hydrogen, alkyl or alkoxy; $R^2$ and $R^3$ taken together represent the carbon atoms necessary to complete a fused benzene ring; $R^4$ and $R^6$ each are selected from hydrogen, alkyl, alkoxy, chloro and fluoro; $R^5$ is hydrogen, alkyl, alkoxy, —$OP^I$ wherein $P^I$ is a protecting group, —N,N-(dialkyl)amino, —N,N-(w-$R^8$-alkyl)$_2$amino wherein $R^8$ is halo or —$OP^{II}$ wherein $P^{II}$ is a protecting group; —$NHCOCH_3$, piperidino, pyrrolidino, N-methylpiperazino, morpholino, thiomorpholino or tetrahydro-2H,4H-1,3,6-dioxazocino; $R^7$ is hydrogen, alkyl, alkoxy or —$OP^{III}$ wherein $P^{III}$ is a protecting group usually the same as $P^I$ or $P^{II}$; $R^6$ and $R^7$ taken together represent the carbon atoms necessary to complete a fused benzene ring provided $R^2$ and $R^3$ are taken separately when $R^6$ and $R^7$ are taken together; and $R^4$, $R^5$ and $R^6$ taken together represents the atoms necessary to complete a fused [ij]quinolizidine ring and X represents the atoms necessary to complete 2,3-dihydronaphtho[1,8-de]-1,2-thiazine-1,1-dioxide or 2,3-dihydrobenz[d]isothioazole-1,1-dioxide.

15. A compound as defined in claim 14 wherein X represents the atoms necessary to complete 2,3-dihydrobenz[d]isothiazole-1,1-dioxide.

16. A compound as defined in claim 14 wherein $R^2$ and $R^3$ are hydrogen.

17. A compound as defined in claim 14 wherein $R^2$ and $R^3$ taken together represent the carbon atoms necessary to complete a fused benzene ring.

18. A compound as defined in claim 14 wherein $R^4$, $R^5$ and $R^6$ taken together represent the atoms necessary to complete a fused [ij]quinolizidine ring and $R^7$ is hydrogen.

19. A compound as defined in claim 14 wherein $R^4$, $R^6$ and $R^7$ are hydrogen.

20. A compound as defined in claim 19 wherein $R^5$ is —N,N-(dialkyl)amino.

21. A compound as defined in claim 19 wherein $R^5$ is —N,N-(w-$R^8$alkyl)$_2$amino.

22. A compound as defined in claim 19 wherein $R^5$ is morpholino.

23. A compound as defined in claim 14 wherein $R^4$ and $R^6$ are hydrogen, $R^5$ is —N,N-(dialkyl)amino and $R^7$ is alkyl.

24. The compound

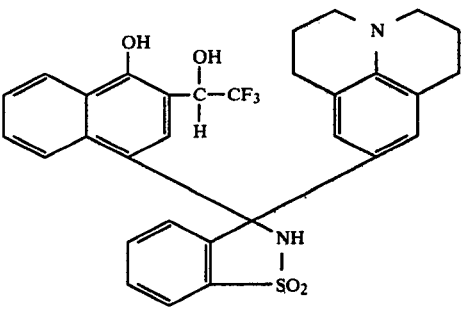

25. The compound

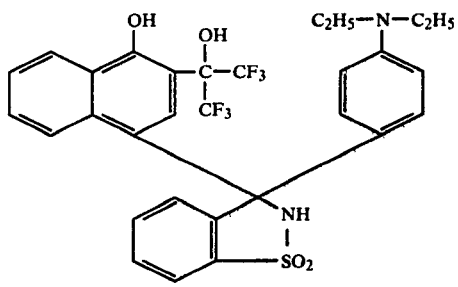

26. The compound

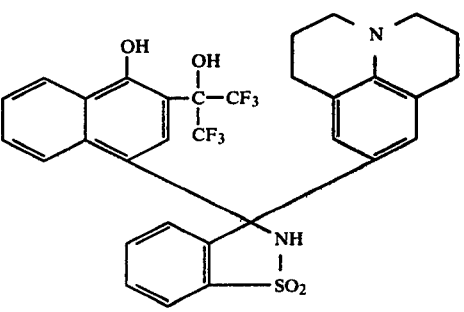

* * * * *